US009554757B2

(12) United States Patent
Steinhauser (10) Patent No.: US 9,554,757 B2
(45) Date of Patent: Jan. 31, 2017

(54) GRADUAL X-RAY FOCAL SPOT MOVEMENTS FOR A GRADUAL TRANSITION BETWEEN MONOSCOPIC AND STEREOSCOPIC VIEWING

(71) Applicant: KONINKLIJKE PHILIPS N.V., Eindhoven (NL)

(72) Inventor: Heidrun Steinhauser, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 133 days.

(21) Appl. No.: 14/385,370

(22) PCT Filed: Mar. 7, 2013

(86) PCT No.: PCT/IB2013/051800
§ 371 (c)(1),
(2) Date: Sep. 15, 2014

(87) PCT Pub. No.: WO2013/140288
PCT Pub. Date: Sep. 26, 2013

(65) Prior Publication Data
US 2015/0071404 A1 Mar. 12, 2015

Related U.S. Application Data

(60) Provisional application No. 61/612,475, filed on Mar. 19, 2012.

(51) Int. Cl.
*A61B 6/02* (2006.01)
*H01J 35/14* (2006.01)
(Continued)

(52) U.S. Cl.
CPC ............ *A61B 6/022* (2013.01); *A61B 6/4021* (2013.01); *A61B 6/4028* (2013.01); *G01N 23/04* (2013.01);
(Continued)

(58) Field of Classification Search
CPC ..... A61B 6/022; A61B 6/4021; A61B 6/4028; H01J 35/06; H01J 35/065; H01J 35/08; H01J 35/10; H01J 35/14
(Continued)

(56) References Cited

U.S. PATENT DOCUMENTS 5,073,914 A 12/1991 Asahina et al.
5,615,279 A 3/1997 Yoshioka et al.
(Continued)

FOREIGN PATENT DOCUMENTS

DE 19953613 A1 5/2001
DE 102008046722 A1 3/2010
(Continued)

*Primary Examiner* — Allen C. Ho (57) ABSTRACT

An X-ray tube includes a cathode, an anode, and a deflection device. The cathode and the anode generate an electron beam that is directed toward a target area of the anode to generate X-ray radiation through electrons of the electron beam impinging the target area. The deflection device controls the electron beam such that the electrons hit the anode at different focal spot positions. The deflection device provides gradual deflection for a stepless transition between monoscopic viewing and stereoscopic viewing. For monoscopic viewing, the X-ray radiation is generated from a single focal spot position. For stereoscopic viewing, the X-ray radiation is generated from two focal spot positions spaced apart in a first stereo-direction transverse to a viewing direction. The deflection device provides gradual deflection for a stereo focal spot position in a second stereo-direction, which is transverse to the first stereo-direction and the viewing direction.

11 Claims, 9 Drawing Sheets (51) Int. Cl.
  *A61B 6/00* (2006.01)
  *H01J 35/06* (2006.01)
  *H01J 35/10* (2006.01)
  *H01J 35/08* (2006.01)
  *H01J 35/30* (2006.01)
  *G01N 23/04* (2006.01)
  *H05G 1/52* (2006.01)

(52) U.S. Cl.
  CPC .............. *H01J 35/065* (2013.01); *H01J 35/08* (2013.01); *H01J 35/10* (2013.01); *H01J 35/14* (2013.01); *H01J 35/30* (2013.01); *H05G 1/52* (2013.01); *A61B 6/4441* (2013.01); *H01J 2235/068* (2013.01)

(58) Field of Classification Search
  USPC .......... 378/41, 122, 125, 136, 137, 143, 144
  See application file for complete search history.

(56) References Cited

U.S. PATENT DOCUMENTS

| | | | | |
|---|---|---|---|---|
| 6,339,635 B1* | 1/2002 | Schardt | ................ | H01J 35/305 378/113 |
| 6,449,333 B1* | 9/2002 | Yamasaki | .............. | A61B 6/022 378/41 |
| 6,456,691 B2* | 9/2002 | Takahashi | .............. | B82Y 10/00 378/122 |
| 6,760,407 B2* | 7/2004 | Price | ....................... | H01J 35/24 378/119 |
| 7,035,371 B2* | 4/2006 | Boese | ..................... | G21K 4/00 378/41 |
| 7,082,182 B2* | 7/2006 | Zhou | ...................... | A61B 6/032 378/10 |
| 7,496,180 B1* | 2/2009 | Subraya | .................. | H01J 35/14 378/137 |
| 7,522,709 B2* | 4/2009 | Masuda | ................. | A61B 6/032 378/124 |
| 7,627,087 B2* | 12/2009 | Zou | ........................ | H01J 1/304 378/122 |
| 7,746,974 B2* | 6/2010 | Shukla | ................... | A61B 6/032 378/4 |
| 7,751,528 B2* | 7/2010 | Zhou | ..................... | A61B 6/025 378/21 |
| 7,809,102 B2* | 10/2010 | Brada | .................... | A61B 6/022 378/20 |
| 7,809,114 B2* | 10/2010 | Zou | ....................... | H01J 1/3048 378/122 |
| 7,826,594 B2* | 11/2010 | Zou | .......................... | H01J 1/30 378/10 |
| 7,852,979 B2* | 12/2010 | Edic | ....................... | A61B 6/032 378/134 |
| 7,869,561 B2* | 1/2011 | Dafni | .................... | A61B 6/032 378/19 |
| 7,869,571 B2* | 1/2011 | Hsieh | .................... | A61B 6/032 378/124 |
| 7,933,378 B2* | 4/2011 | Proksa | ................... | A61B 6/032 378/9 |
| 7,949,089 B2* | 5/2011 | Dafni | .................... | A61B 6/022 378/6 |
| 7,978,816 B2* | 7/2011 | Matsuura | ............... | A61B 6/032 378/62 |
| 8,094,773 B2* | 1/2012 | Boese | .................... | A61B 6/025 378/21 |
| 8,180,017 B2* | 5/2012 | Forthmann | ............ | A61B 6/032 378/156 |
| 8,520,803 B2* | 8/2013 | Behling | .................. | H01J 35/10 378/124 |
| 8,537,965 B2* | 9/2013 | Dafni | .................... | A61B 6/032 378/4 |
| 8,625,743 B1* | 1/2014 | Caiafa | .................... | H01J 35/14 378/112 |
| 8,693,638 B2* | 4/2014 | Dafni | .................... | A61B 6/032 378/124 |
| 8,712,007 B2* | 4/2014 | Flohr | .................... | A61B 6/032 378/11 |
| 8,712,015 B2* | 4/2014 | Caiafa | .................... | H01J 35/18 378/110 |
| 8,817,947 B2* | 8/2014 | Vedantham | ........... | A61B 6/022 378/21 |
| 8,908,826 B2* | 12/2014 | Bernhardt | .............. | A61B 6/022 378/42 |
| 9,036,777 B2* | 5/2015 | Ohishi | ................... | A61B 6/022 378/41 |
| 9,277,893 B2* | 3/2016 | Tsukagoshi | ........... | A61B 6/022 |
| 2009/0161815 A1 | 6/2009 | Grass | | |
| 2010/0040196 A1 | 2/2010 | Zhang et al. | | |
| 2010/0067662 A1 | 3/2010 | Pietig et al. | | |
| 2015/0043714 A1* | 2/2015 | Steinhauser | ........... | A61B 6/022 378/62 |

FOREIGN PATENT DOCUMENTS

| | | |
|---|---|---|
| EP | 0144272 A1 | 6/1985 |
| JP | 201250517 A | 3/2013 |
| WO | 2011083416 A1 | 7/2011 |

* cited by examiner

GRADUAL X-RAY FOCAL SPOT MOVEMENTS FOR A GRADUAL TRANSITION BETWEEN MONOSCOPIC AND STEREOSCOPIC VIEWING

This application is the U.S. National Phase application under 35 U.S.C. §371 of International Application No. PCT/IB2013/051800, filed on Mar. 7, 2013, which claims the benefit of U.S. Provisional Application No. 61/612,475 filed on Mar. 19, 2012. These applications are hereby incorporated by reference herein.

FIELD OF THE INVENTION

The present invention relates to an X-ray tube for monoscopic and stereoscopic viewing, an X-ray imaging system for monoscopic and stereoscopic viewing, a method for providing spatial viewing of an object, a computer program element and a computer readable medium.

BACKGROUND OF THE INVENTION

For providing depth information of an object, X-ray stereo imaging is used, for example in medical imaging. However, it has been found that, although stereo imaging provides useful depth information, the user, for example a physician, maintains and sometimes even prefers monoscopic viewing techniques. The switching to stereo imaging is hence sometimes avoided. Thus, additional depth information is sometimes not made visible to the user. US 2010/0067662 describes a stereo rotating anode X-ray tube.

SUMMARY OF THE INVENTION

Hence, there may be a need to provide an improved fluent work flow for X-ray viewing with an improved visual perception of depth information.

The object of the present invention is solved by the subject-matter of the independent claims, wherein further embodiments are incorporated in the dependent claims.

It should be noted that the following described aspects of the invention apply also for the X-ray tube for monoscopic and stereoscopic viewing, the X-ray imaging system for monoscopic and stereoscopic viewing, and the method for providing spatial viewing of an object, as well as the computer program element and the computer readable medium.

According to a first aspect of the present invention, an X-ray tube for monoscopic and stereoscopic viewing is provided, that comprises a cathode arrangement, an anode, and control means. The cathode arrangement and the anode are provided to generate an electron beam from the cathode arrangement towards a target area of the anode to generate X-ray radiation by electrons impinging on the target area. The control means are provided to control the electron beam such that the electrons hit the anode at different target spots. The control means are configured to provide gradual variation of an impinging direction of the electrons for a stepless transition between monoscopic and stereoscopic viewing. In the monoscopic viewing, X-ray radiation is generated from a single focal spot position, and in the stereoscopic viewing, X-ray radiation is generated from two focal spot positions spaced apart from each other in a first stereo-direction transverse to a viewing direction.

The term "gradual variation for a stepless transition" refers to a continuous change of the focal spot position such that a user viewing the respective images is facilitated in the perception of the continuously changing point of views, namely a point of view for a monoscopic viewing and the respective stereoscopic viewing, as is the case from two spaced apart focal spots. The term "gradual" relates in particular to the perception of the user and thus comprises relatively small steps for the movement of the focal spot, which stepwise change, although not literally being a gradual movement, is also subsumed by the term "gradual".

The term "impinging direction" comprises e.g. an impinging angle of the electron beam.

For example, the gradual variation is a gradual deflection of the electron beam. In a further example, an electron beam with a varying effective direction is generated, for example by a number of variable electron sources.

For example, the control means are measures for deflection of the electron beam.

According to an exemplary embodiment, the control means are configured to provide gradual variation for at least one stereo focal spot also in a second stereo-direction, which is transverse to the first stereo-direction and transverse to the viewing direction.

According to an exemplary embodiment, the cathode arrangement comprises a single cathode and the control means are deflection means provided to deflect the electron beam.

According to a further exemplary embodiment, the cathode arrangement comprises a plurality of Carbon Nanotube emitters, which Carbon Nanotube emitters are configured to provide an electron beam with different focal spot positions, and the control means are provided as a control arrangement of the Carbon Nanotube emitters.

According to an exemplary embodiment, the anode is provided with an inclined focal track area providing different heights for the focal spot positions, and the focal track area is provided with an increasing inclination degree.

According to a second aspect of the present invention, an X-ray imaging system for monoscopic and stereoscopic viewing is provided, comprising an X-ray source, an X-ray detector, and a processing unit. The X-ray source is an X-ray tube according to one of the above-mentioned examples. The X-ray detector is configured to provide X-ray detection signals to the processing unit. The processing unit is configured to compute monoscopic and stereoscopic X-ray image data based on the X-ray detection signals.

According to a third aspect of the present invention, a method for providing spatial viewing of an object is provided, comprising the following steps:
a) generating an electron beam from a cathode arrangement towards a target area of an anode;
b) controlling the electron beam such that the electron beam hits the anode at different target spots;
c) generating X-ray radiation by the electron beam impinging on the target area, wherein the X-ray radiation is provided with different focal spots for monoscopic and stereoscopic X-ray imaging; and
d) providing image data of the object with a gradual transition between monoscopic and stereoscopic viewing.

The controlling in step b) is provided as gradual variation of an impinging direction of the electrons such that a stepless transition between monoscopic and stereoscopic viewing is provided. It is noted that the term "stepless transition" relates to the perception of a user. In the monoscopic viewing, X-ray radiation is generated from a single focal spot position, and in the stereoscopic viewing, X-ray radiation is generated from two focal spot positions spaced apart from each other in a first stereo-direction transverse to a viewing direction.

For example, the controlling in step b) is a deflection and the gradual variation is a gradual deflection.

The electron beam may be provided by several electron sub-beams.

The gradual variation of an impinging direction of the electrons comprises an electron beam hitting different positions, i.e. varying positions of the focal track. The different impinging directions may comprise parallel directions hitting different positions. The different impinging directions may also comprise different angles of the directions.

According to an aspect of the present invention, a steady increase or decrease of the focal spot separation is provided for a transition between monoscopic and stereoscopic imaging and vice versa. Thus, instead of simply switching between monoscopic and stereoscopic imaging, the gradual transition between the two types of view, i.e. the gradual transition between mono and stereo viewing, helps the visual perception of live depth information and thus improves the user friendliness and acceptance. In particular the gradual transition provided a fluent work flow. According to an aspect of the present invention, the gradual transition also allows an adaption or adjustment of the intensity of the stereo effect, thus providing the possibility to take into account respective favorite settings of different personnel.

These and other aspects of the invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
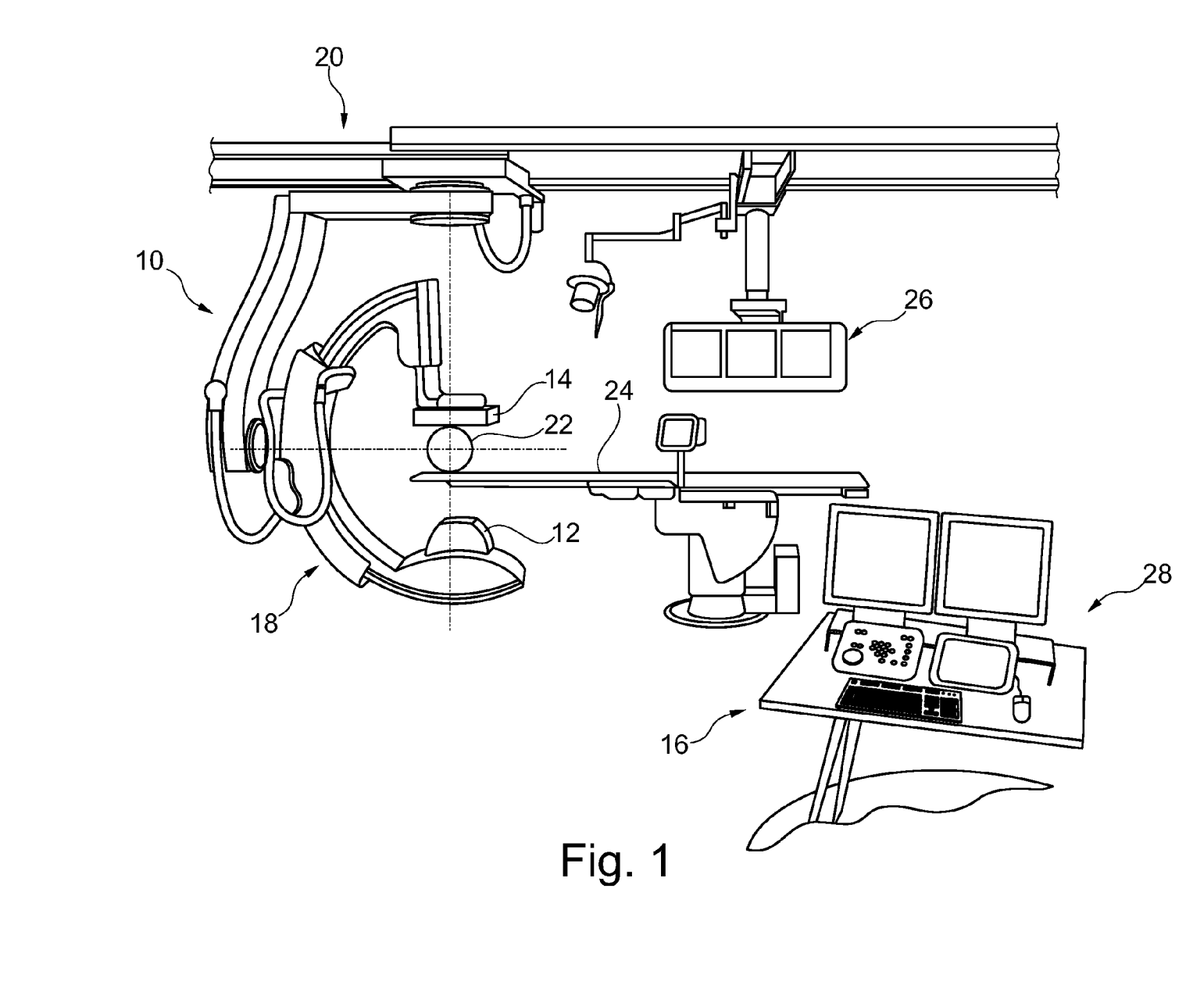
FIG. 1 shows a C-arm arrangement as an example for an X-ray imaging system according to the present invention.

FIG. 1 shows an X-ray imaging system 10 for monoscopic and stereoscopic viewing. The X-ray imaging system 10 is provided with an X-ray source 12, an X-ray detector 14, and a processing unit 16. The X-ray source 12 and the X-ray detector 14 are arranged on a C-arm structure 18 mounted to a movable support structure 20 allowing rotational movements around an object of interest, for example a patient, wherein the object is indicated with a circular structure only, with reference numeral 22. Further, a support structure, for example a patient table 24, is provided for supporting the object 22. Still further, a display arrangement 26 is shown, as well as an interface and control arrangement 28 shown in the foreground.

The X-ray source 12 is an X-ray tube 30 as described in more detail below with reference to following drawings. The X-ray detector 14 is configured to provide X-ray detection signals to the processing unit 16, and the processing unit 16 is configured to compute monoscopic and stereoscopic X-ray image data based on the X-ray detection signals.

It must be noted that the X-ray imaging system 10 is shown as a C-arm type examination apparatus as an example only. Of course, other X-ray imaging systems, for example X-ray imaging systems where the X-ray source 12 and the X-ray detector 14 are mounted to robotic arms, or X-ray imaging systems with fixedly mounted X-ray source 12 and X-ray detector 14, are also provided.

Figure 2:
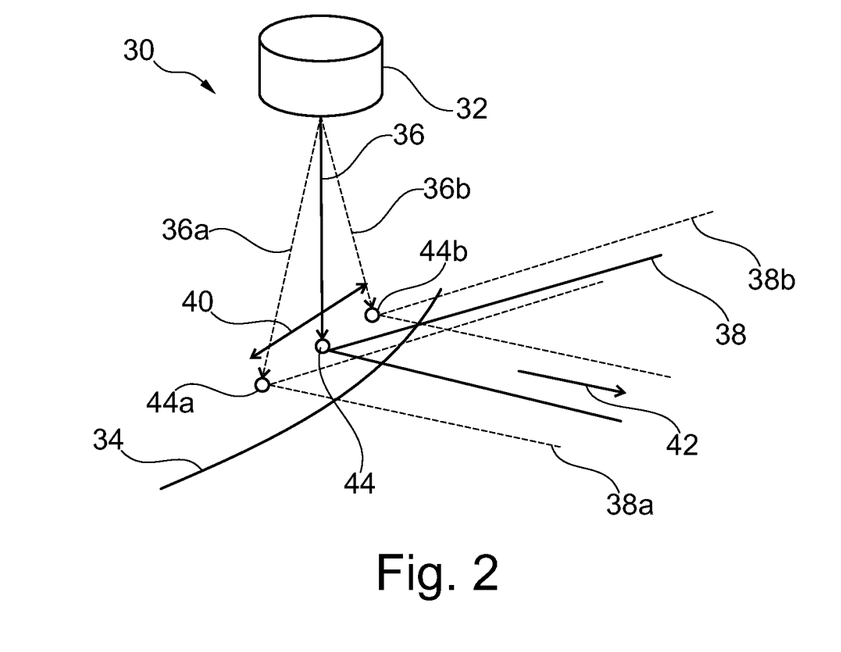
FIG. 2 shows a perspective schematic view of an X-ray tube according to an example of the present invention.

FIG. 2 shows a schematic perspective view of the X-ray tube 30. The X-ray tube 30 is provided for monoscopic and stereoscopic viewing and comprises a cathode arrangement 32, an anode 34, and control means, the latter being described further below.

The cathode arrangement 32 and the anode 34 are provided to generate an electron beam 36 from the cathode arrangement 32 towards a target area of the anode 34 to generate X-ray radiation 38 by electrons impinging on the target area.

The control means are provided to control the electron beam 36 such that the electrons hit the anode 34 at different target spots, wherein the control means are configured to provide gradual variation of an impinging direction of the electrons for a stepless transition (see also FIG. 7) between monoscopic and stereoscopic viewing.

In the monoscopic viewing, X-ray radiation 38 is generated from a single focal spot position, and in the stereoscopic viewing, X-ray radiation 38 is generated from two focal spot positions spaced apart from each other in a first stereo-direction 40 transverse to a viewing direction 42.

For example, the electron beam 36 is controlled such that it is moved to either side, as indicated with dotted lines 36a and 36b. Thus, the electron beam 36 hits the anode 34 at different target spots, namely a middle focal spot 44 and a first sideways arranged focal spot 44a and a second sideways arranged focal spot 44b. Consequently, the X-ray radiation 38 is generated for the middle focal spot position 44, and a further X-ray radiation is indicated with reference numeral 38a to first sideways focal spot 44a, and a second X-ray radiation 38b for the second sideways arranged focal spot 44b. For example, for the monoscopic viewing, the middle focal spot 44 can be provided, and for the stereoscopic viewing, the sideways arranged focal spots 44a and 44b can be used. Of course, other positions of the focal spots and the respective combinations can also be provided. For example, one of the sideways arranged focal spots 44a and 44b can be used together with the middle focal spot 44 for stereoscopic viewing, and the other one of the sideways arranged focal spots 44a and 44b can then be used for the monoscopic viewing.

Further, it must be noted that it is a central aspect of the present invention to provide gradual transition between the different focal spots in their positions, which will be described further in relation with FIG. 7. Thus, the focal spot positions in FIG. 2 are only indicating some positions of the transitional movement of the focal spots.

Figure 3:
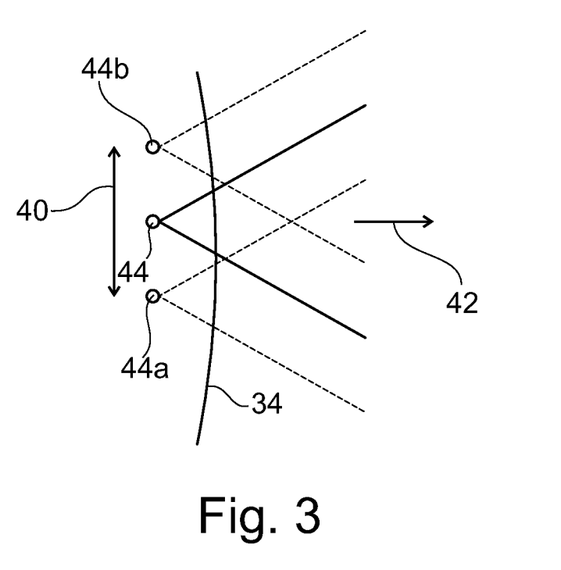
FIG. 3 shows a top view of the X-ray tube of FIG. 2.

FIG. 3 shows a top view of the anode 34 and the respective focal spot positions. Same reference numerals are used for the same features.

Figure 4:
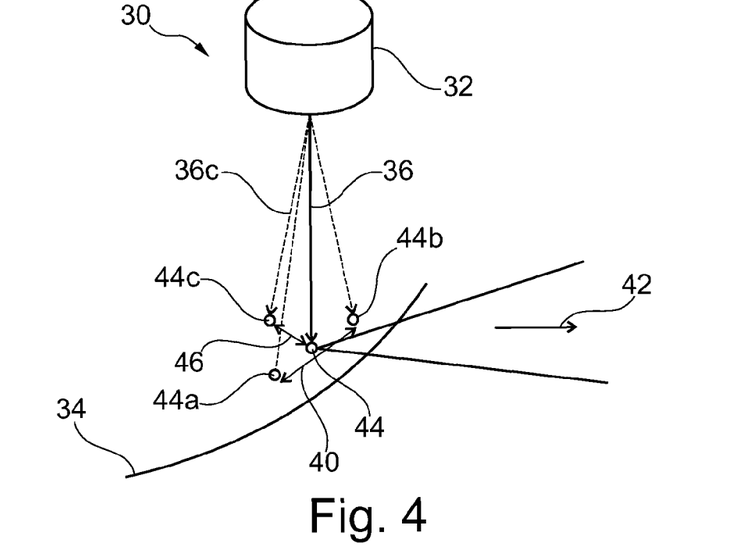
FIG. 4 shows another example of an X-ray tube according to the present invention in a perspective view.
Figure 5:
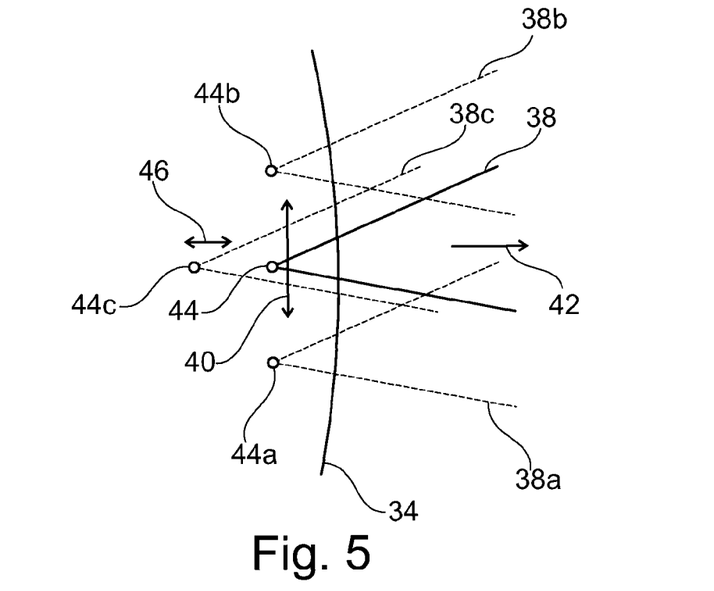
FIG. 5 shows a top view of the X-ray tube of FIG. 4.

According to a further example, shown in FIGS. 4 and 5, the control means are configured to provide gradual variation for at least one stereo focal spot also in a second stereo-direction 46, which is transverse to the first stereo-direction 40 and transverse to the viewing direction 42.

For a better visibility, the variation, for example deflection, in the second stereo-direction 46 is indicated for the middle focal spot 44 only. The gradual variation in the second stereo-direction 46 results in a further varied, i.e. deflected or offset focal spot 44c. Further, the respective controlled electron beam 36 is indicated with reference numeral 36c.

With respect to the at least one stereo focal spot, i.e. either one of the two stereo focal spots or both stereo focal spots, respectively offset or moved positions would be provided.

FIG. 5 shows a top view of the focal spots arrangement of FIG. 4.

Figure 6:
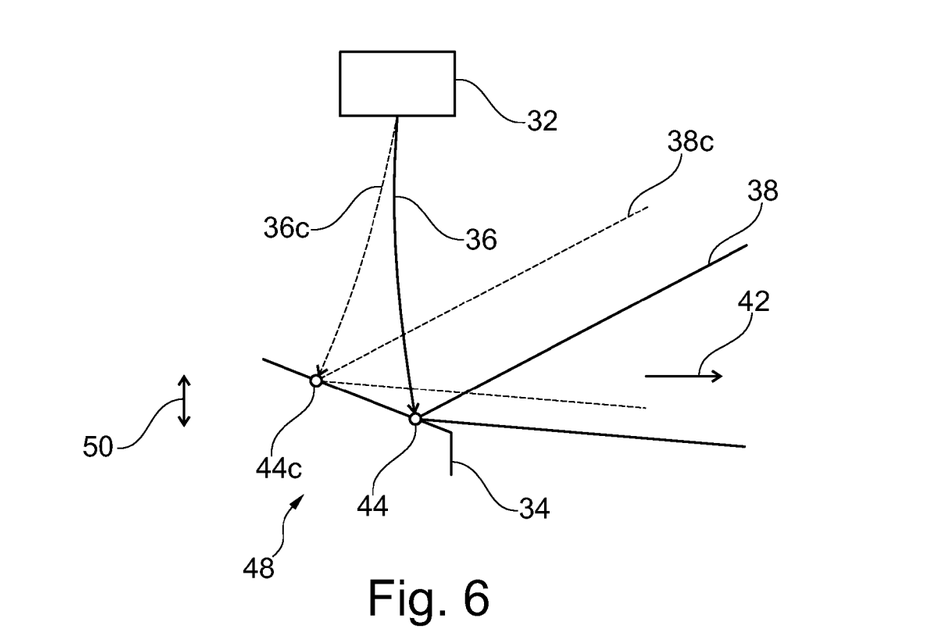
FIG. 6 shows a schematic cross-section of FIG. 4.

FIG. 6 shows a cross-sectional view of the arrangement of FIG. 4. As can be seen, the electron beam 36 can be gradually varied, e.g. deflected towards the left resulting in the above-mentioned electron beam 36c, impinging on the anode 34 at focal spot position 44c. This results in the X-ray radiation 38c.

The anode 34 is provided with an inclined target area 48, resulting in a vertical offset 50 as the effective second stereo-direction 46, transverse to the viewing direction 42, and also transverse to the first viewing direction 40 (see FIG. 5).

The control means are configured to provide the gradual variation such that, in stereoscopic viewing, a connection line between the first focal spot position and the second focal spot position may be arranged on a common plane with the viewing direction (not further shown in the figures). Of course, a combination of first and second variation direction, e.g. first and second deflection direction is also provided.

The first stereo-direction 40 is also referred to as horizontal direction, and the second stereo-direction 46 is also referred to vertical direction.

Figure 7:
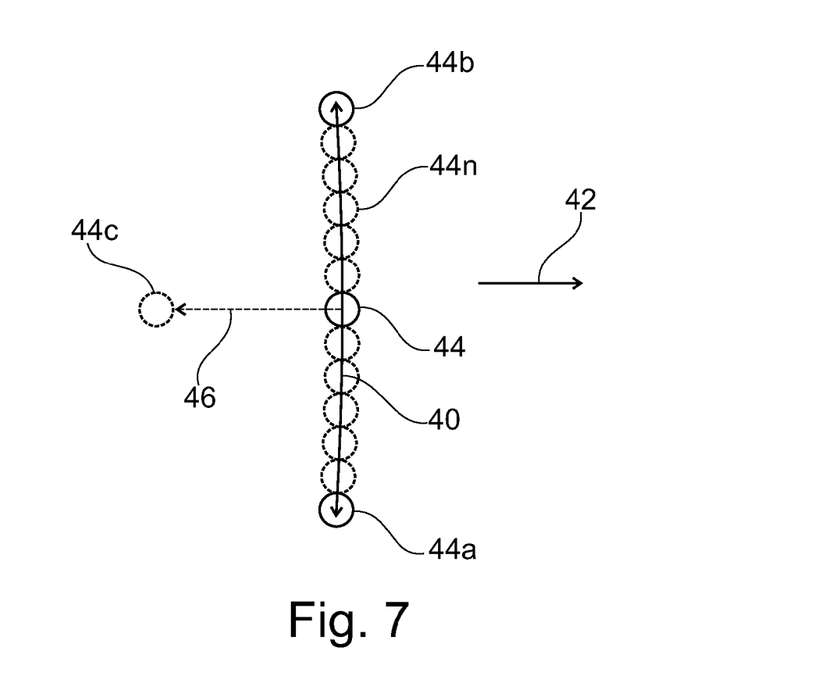
FIG. 7 shows an example for a gradual variation of the focal spot according to the present invention.

FIG. 7 indicates in a top view of the focal spot positions that, according to the present invention, a gradual variation is provided, resulting in a plurality of different focal spot positions 44n, of which the above-mentioned focal spot positions, 44, 44a, and 44b are only examples. The first stereo-direction 40 is also indicated, as well as the viewing direction 42. In case of providing a gradual variation also in the second stereo-direction 46, respective target spot positions are provided between the focal spot position 44 and the focal spot position 44c (not further indicated).

Thus, the gradual variation according to the present invention comprises a steady increase or decrease of the focal spot separation.

Figure 8:
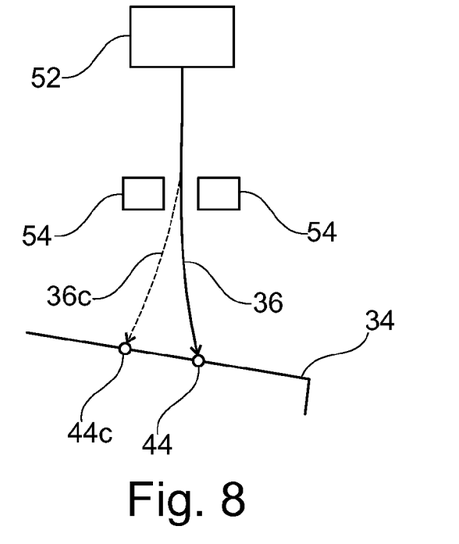
FIG. 8 shows a further example of an X-ray tube according to the present invention in a schematic cross-section.

FIG. 8 shows a further embodiment of the X-ray tube 30, wherein the cathode arrangement comprises a single cathode 52 and the control means are provided as deflection means 54, provided to deflect the electron beam 36. For example, the electron beam 36 and the electron beam 36c are shown, resulting in the above-mentioned focal spot positions 44 and 44c on the anode 34.

For example, the variation, i.e. the deflection is provided electrostatically or electromagnetically.

Figure 9:
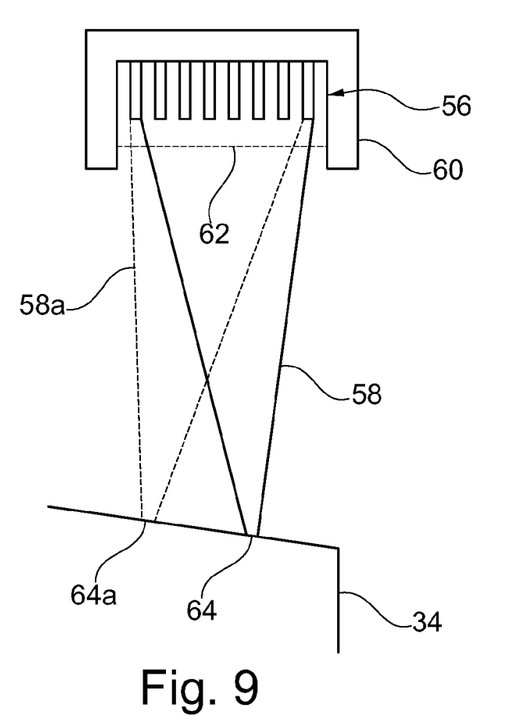
FIG. 9 shows a further example of an X-ray tube according to the present invention in a cross-section.

FIG. 9 shows a further example of the X-ray tube 30, wherein the cathode arrangement comprises a plurality of Carbon Nanotube emitters 56, which are configured to provide an electron beam 58 with different focal spot positions. As an example only, a second shape/direction of the electron beam 58 is indicated with dotted lines and reference numeral 58a. Of course, other shapes/directions are also provided. The control means are provided as a control arrangement of the plurality of Carbon Nanotube emitters 56. For example, steering or guiding electrodes 60 are provided in addition with a gate structure 62, thus allowing to control the plurality of Carbon Nanotube emitters 56 such that different focal spot positions 64, 64a can be hit by the respective electron beam 58 in order to generate X-ray radiation (not further shown).

Figures 10, 11:
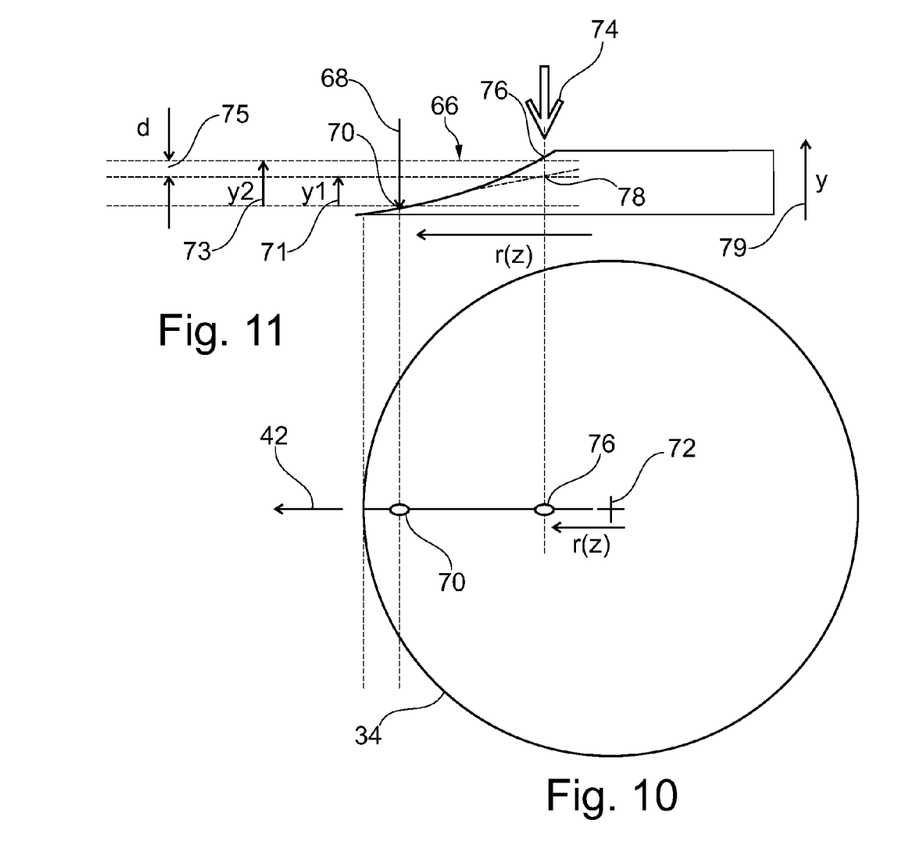
FIG. 10 shows a further example of an X-ray tube according to the present invention in a top view.
FIG. 11 shows a cross-section of the X-ray tube of FIG. 10.

FIG. 10 shows a top view of the anode 34, for example a rotating anode. The anode 34 is provided with an inclined focal track area 66, as shown in FIG. 11. Thus, different heights are provided for the focal spot positions. According to the present invention, the inclined focal track area 66 is provided with an increasing inclination degree, as shown in FIG. 11.

It must be noted that the feature of the anode 34 being a rotating anode is also provided in combination with the other embodiments, e.g. FIGS. 1 to 9. However, with respect, to FIGS. 10, 11, 12 and 14, it is also provided to have a non-rotating anode 34 with similar features.

The term "inclination of the focal track" relates to an inclination in the relation to the viewing direction 42. The inclination degree may be decreasing in the viewing direction 42. For example, the surface has a concave structure or form in a cross-section in viewing direction 42.

The viewing direction 42 is also indicated with "r". A first arrow 68 indicates a first electron beam hitting the anode 34 at a first focal spot position 70. For example, a first and a second focal spot can be provided on both sides of the centre point of the anode 34, which centre point is indicated with reference numeral 72. A second arrow 74 indicates a second electron beam, resulting in a respective second focal spot position 76. In case of a steadily, i.e. continuously or linearly inclining target surface area on the anode 34, this would result in a crossing point of the respective lines, as indicated with reference numeral 78. However, since the inclination is having an increasing degree, the resulting second focal spot position 76 is higher in y-direction 79, in relation to the rotating axis of the anode 34, thus resulting in an additional offset in the y-direction 79.

Of course, also an increasing in the viewing direction 42 can be provided, i.e. an increasing degree of inclination of the disk's cross section profile from a point closer to the axis of rotation towards the outer edge of the anode 34, resulting in an additional offset in the y-direction 79, i.e. in the direction of the axis of rotation of the anode 34. This provides the advantage that for providing a respective focal spot height position (variation/deflection in y-direction 79), only a smaller offset in radial direction must be provided by controlling, e.g. deflecting the electron beam.

The first mark 70 represents a first focal spot position on the so-to-speak lower portion of the inclined focal track area 66. The second mark 76 represents the position of a second focal spot position in order to achieve the height of the intersection point. A first arrow 71 represents the height y1 that would be achieved in case of a continuous inclination degree. A second arrow 73 represents the height y2 that is achieved due to the increasing inclination degree. Thus, the increasing inclination degree provides a delta 75 plus in height d without any further extension in r-direction. In other words, the increasing inclination degree provides a reduced range of inclination with respect to providing similar focal spot positions (y-variations/-deflections).

Figure 12:
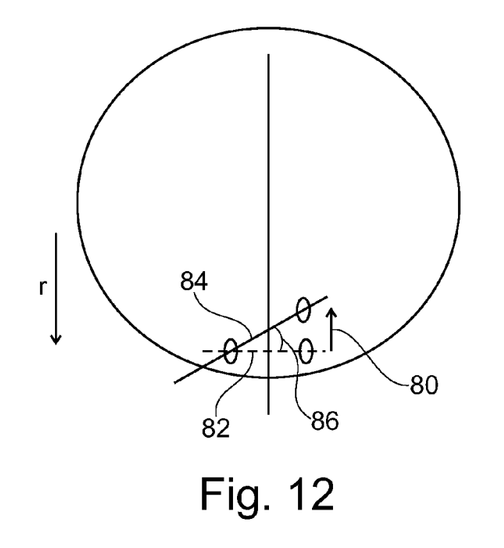
FIG. 12 shows a further example of an X-ray tube according to the present invention.

As shown in FIG. 12, it is also possible to provide a gradual variation, indicated with arrow 80, only for one of two focal spot positions, thus providing a tilt of the stereo-direction. This is indicated with a connection line 82, shown in a dotted manner, connecting the none-tilted stereo focal spot positions, in relation to the resulting tilted stereo-direction, indicated with a connection line 84 in a straight line. Thus, a tilting angle 86 results.

Figure 13:
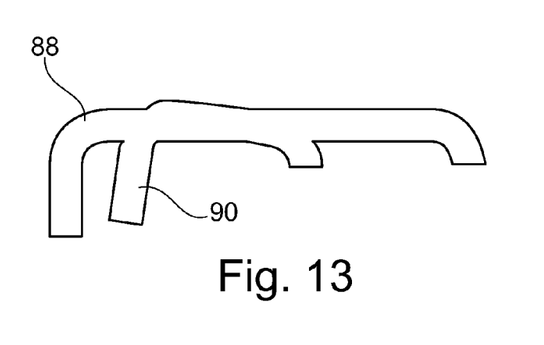
FIG. 13 schematically illustrates the resulting image of the example of FIG. 12.

As an effect, as shown in FIG. 13, a first vessel segment 88 and a second vessel segment 90 are also tilted in relation to each other due to the respective spatial arrangement. Thus, the two vessel segments 88 and 90 can be virtually separated from each other by the user in an enhanced and facilitated manner.

In other words, the gradual variation can be adapted separately, i.e. individually, for each focal spot position, for example for the first and/or second stereo-direction 40 and/or 46.

Figure 14:
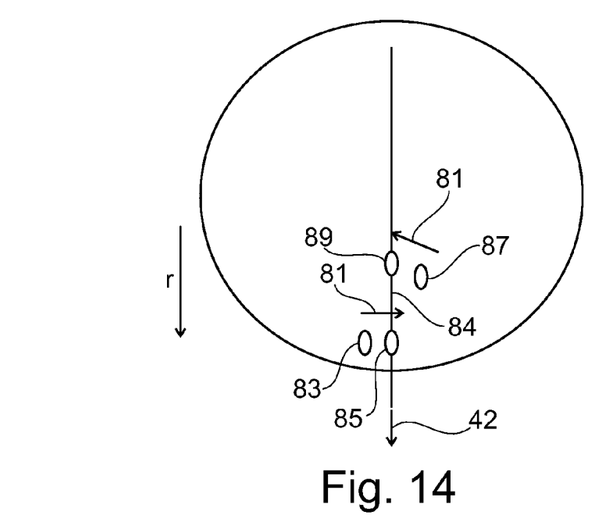
FIG. 14 shows a further example of an X-ray tube according to the present invention.

As shown in FIG. 14, with a gradual variation it is also possible to shift or rotate the connection line from a standard stereo view in the first stereo-direction 40, in which the connection line is arranged on a plane perpendicular to the viewing direction 42, to the second stereo-direction 46, in which the connection line is arranged in a plane of the viewing direction 42. Thus, the connection line 84 is provided aligned with the viewing direction 42 in the top plan view of the focal spot positions of FIG. 14. The first focal spot position is gradually moved from a first position 83 to a second position 85 in a so-to-speak first shifting movement to the right side; the second focal spot position is gradually moved from a first position 87 to a second position 89 in a so-to-speak second shifting movement to the slightly upper left side. Both shifting movements are indicated with an arrow 81.

As indicated above, switching between monoscopic and stereoscopic imaging is provided as a gradual transition between the two viewing modes by a steady increase or decrease of the focal spot separation in order to give a fluent work flow. Thus, the visual perception of live depth information is supported.

An additional gradual X-ray focal spot movement can also improve the stereo viewing itself. X-ray stereo imaging gives mainly live depth information in a horizontal stereo-direction. By an additional movement of the two stereo focal spot positions during stereo viewing, or a movement of only one of the two stereo focal spot positions, the live depth information in vertical direction is increased. For example, a result is that the distinction between two horizontal blood vessels overlapping each other in the X-ray image is improved. Moreover, the extra movement also improves the stereo perception itself. Besides a synchronized vertical movement of both stereo focal spot positions, it is also provided to tilt the stereo-direction by moving one focal spot in a mainly vertical direction. It is noted that the term "vertical" relates to the resulting or effective focal spot movement, for example which is the case in an inclined focal track area.

Figure 15:
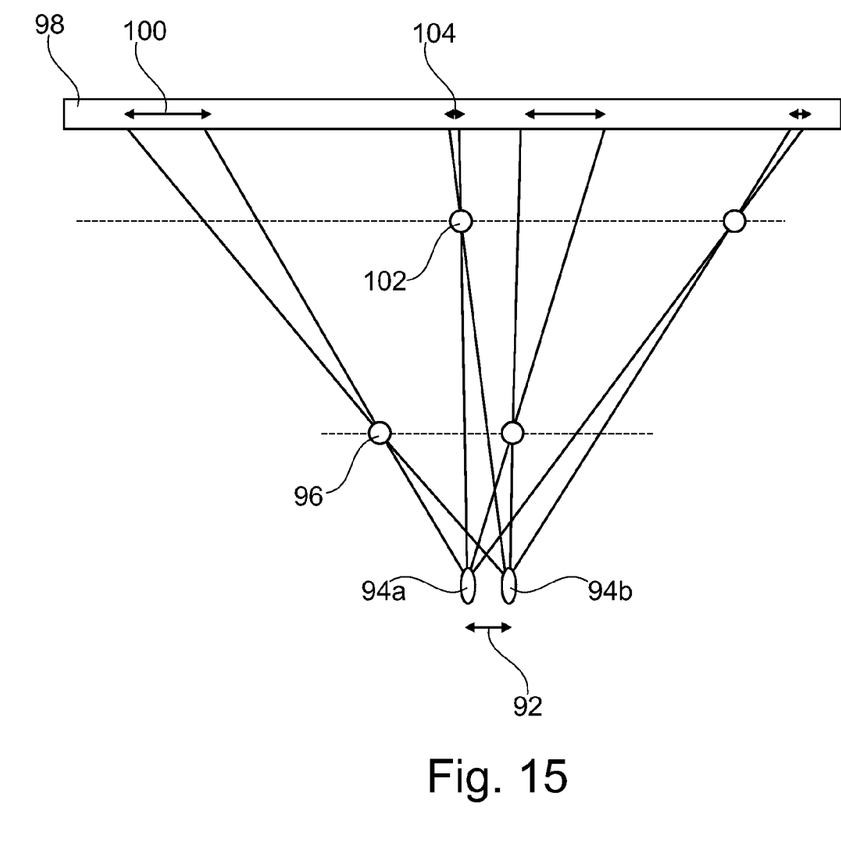
FIG. 15 shows the resulting effect of an exemplary embodiment of an X-ray tube according to the present invention.

As shown in FIG. 15, a gradual adaption of the focal spot separation, indicated with reference numeral 92, can be provided. By so-to-speak gradually or continuously changing the distance of the two stereo focal spot positions 94a and 94b, an object 96 being provided closer to the focal spot is detected by an X-ray detector 98 with a larger resulting movement 100 than an object 102 being arranged farther away from the focal spot positions 94a and 94b, as indicated for an object 102, resulting in a smaller detectable movement 104.

For example, a resulting image would show objects closer to the focal spot positions 94a and 94b in a blurred manner, whereas objects being arranged closer to the X-ray detector 98 would appear sharper in the image.

This would also improve the understanding by the user on which blood vessel, for example, is behind other blood vessels in case of horizontal crossing.

Figure 16:
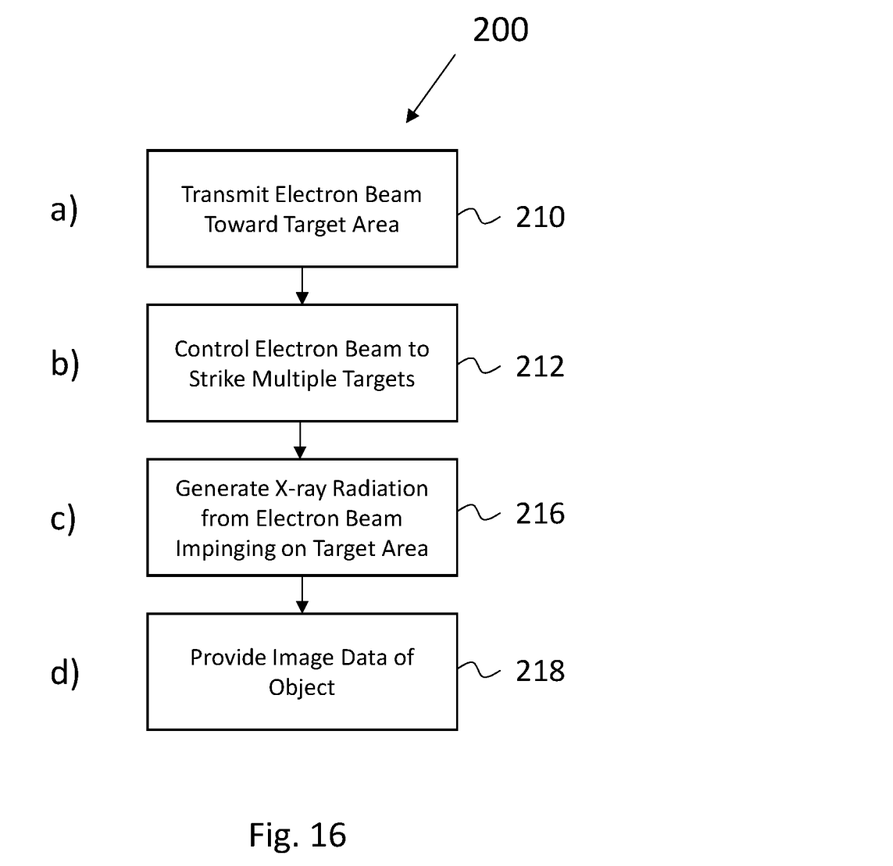
FIG. 16 shows basic steps of a method for providing spatial viewing of an object according to an exemplary embodiment of the present invention.

FIG. 16 shows a method 200 for providing spatial viewing of an object, comprising (b-following steps: In a first step 210, an electron beam 36 is generated from a cathode arrangement 32 towards a target area of an anode 34. In a second step 212, the electron beam 36 is controlled such that the electron beam 36 hits the anode 34 at different focal spot positions. The control is provided as gradual variation of an impinging direction of the electron beam 36 such that a stepless transition 214 between monoscopic and stereoscopic viewing is achieved. In the monoscopic viewing, X-ray radiation is generated from a single focal spot position, and in the stereoscopic viewing, X-ray radiation is generated from two focal spot positions spaced apart from each other in a first stereo-direction 40 transverse to a viewing direction 42. In a third step 216, X-ray radiation is generated by the electron beam 36 impinging on the target area. The X-ray radiation is provided with different focal spot positions for monoscopic and stereoscopic X-ray imaging. In a fourth step 218, image data of the object is provided with a gradual transition between monoscopic and stereoscopic viewing.

For example, the controlling in step 212 is a deflection and the gradual variation is a gradual deflection.

The first step 210 is also referred to as step a), the second step 212 as step b, the third step 216 as at c), and the fourth step 218 as step d).

According to a further example (not shown), the gradual variation in step h) comprises gradual variation for at least one stereo focal spot position also in a second stereo-direction 46, which is transverse to the first stereo-direction 40 and transverse to the viewing direction 42.

According to a further example (also not further shown), the gradual variation in step b) comprises, in stereoscopic viewing, a shifting of a connection line between the first focal spot position and the second focal spot position such that the connection line is arranged on a common plane with the viewing direction 42.

According to the present invention, instead of a simply switch between stereoscopic viewing and monoscopic viewing, a smooth transition is provided by controlling or deflecting the electron beam 36 such that, for example, when starting from monoscopic viewing, the single focal spot position is smoothly transferred into two focal spot positions for the stereoscopic viewing, wherein the so-to-speak separation of the two focal spot positions, which are initially positioned at the same position for the monoscopic viewing, are increasingly arranged spaced apart from each other for the stereoscopic viewing. Thus, a user who is very comfortable with the so-to-speak standard monoscopic viewing is seamlessly guided towards the stereoscopic viewing. In other words, there is not harsh shift between the two types of viewing which always mean an additional adaption phase for the user who first has to adapt this understanding of the image shown. Of course, similar is also the case when viewing stereoscopic image and then providing a smooth transition to monoscopic viewing according to the present invention. Hence, the provision of the additional spatial information as provided in the stereoscopic viewing can be integrated in the work flow in a facilitated manner and situations are avoided where a user, for example a surgeon, has to adapt his reading of the provided image to the new way, i.e. to monoscopic or stereoscopic viewing. As a further aspect, it is noted that when performing a transition from monoscopic to stereoscopic viewing, firstly the user is provided with so-to-speak simple attenuation information, and so far no spatial information. However, during the transition to stereoscopic viewing, additional spatial information is becoming visible successively in dependence from the increasing width of the two focal spot positions. Thus, the user so-to-speak sees a growing spatial depth information, which improves the capability of the user to read X-ray images. The spatial information, as being provided in an increasing manner according to the present invention, is presented in an intuitive way enhancing the understanding of the current situation.

The invention claimed is:

1. An X-ray tube for monoscopic and stereoscopic viewing, the X-ray tube comprising:
a cathode arrangement;
an anode; and
a deflection device, wherein:
the cathode arrangement and the anode generate an electron beam from the cathode arrangement and direct the electron beam towards a target area of the anode to generate X-ray radiation through electrons of the electron beam impinging on the target area;
the deflection device controls the electron beam such that the electrons hit the anode at different focal spot positions;
the deflection device provides gradual deflection for a stepless transition between the monoscopic viewing and the stereoscopic viewing;
in the monoscopic viewing, the X-ray radiation is generated from a single focal spot position,
in the stereoscopic viewing, the X-ray radiation is generated from two focal spot positions spaced apart from each other in a first stereo-direction transverse to a viewing direction, and
the deflection device provides gradual deflection for a stereo focal spot position in a second stereo-direction, which is transverse to the first stereo-direction and transverse to the viewing direction.

2. The X-ray tube according to claim 1, wherein the deflection device provides the gradual deflection such that, in the stereoscopic viewing, a connection line between a first focal spot position and a second focal spot position of the two focal spot positions is arranged on a common plane with the viewing direction.

3. The X-ray tube according to claim 1, wherein:
the cathode arrangement comprises a single cathode; and
the deflection device deflects the electron beam.

4. The X-ray tube according to claim 1, wherein:
the cathode arrangement comprises a plurality of carbon nanotube emitters, which are configured to generate the electron beam with the different focal spot positions; and
the deflection device controls the plurality of carbon nanotube emitters.

5. The X-ray tube according to claim 1, wherein a portion of the target area of the anode is inclined so as to provide different heights for the focal spot positions.

6. A method for providing spatial viewing of an object, the method comprising:

a) generating an electron beam with a cathode arrangement and directing the electron beam toward a target area of an anode;
b) deflecting the electron beam, with a deflection device, such that the electron beam hits the anode at different focal spot positions; wherein deflecting the electron beam comprises providing a gradual deflection of the electron beam such that a stepless transition between monoscopic viewing and stereoscopic viewing is provided;
c) generating X-ray radiation through electrons of the electron beam impinging on the target area; wherein:
the X-ray radiation is provided with different focal spot positions for the monoscopic viewing and the stereoscopic viewing; and
in the monoscopic viewing, the X-ray radiation is generated from a single focal spot position, and
in the stereoscopic viewing, the X-ray radiation is generated from two focal spot positions spaced apart from each other in a first stereo-direction transverse to a viewing direction; and
d) providing image data of the object with a gradual transition between the monoscopic viewing and the stereoscopic viewing.

7. The method according to claim 6, wherein the gradual deflection in step b) comprises gradual deflection for at least one stereo focal spot position in a second stereo-direction, which is transverse to the first stereo-direction and transverse to the viewing direction.

8. The method according to claim 6, wherein the gradual deflection in step b) comprises, in the stereoscopic viewing, a shift of a connection line between a first focal spot position and a second focal spot position of the two focal spot positions such that the connection line is arranged on a common plane with the viewing direction.

9. The method of claim 6, wherein:
the cathode arrangement comprises a plurality of carbon nanotube emitters that provide the electron beam with the different focal spot positions, and
the deflection device controls the carbon nanotube emitters.

10. The method of claim 6, wherein a portion of the target area of the anode is inclined so as to provide different heights for the focal spot positions.

11. An X-ray imaging system for monoscopic and stereoscopic viewing, the system comprising:
an X-ray tube comprising a cathode arrangement, an anode, and a deflection device, wherein:
the cathode arrangement and the anode generate an electron beam from the cathode arrangement and direct the electron beam toward a target area of the anode so as to generate X-ray radiation through electrons of the electron beam impinging on the target area,
the deflection device controls the electron beam such that the electrons hit the anode at different focal spot positions,
the deflection device provides gradual deflection for a stepless transition between the monoscopic viewing and the stereoscopic viewing of an object,
in the monoscopic viewing, the X-ray radiation is generated from a single focal spot position,
in the stereoscopic viewing, the X-ray radiation is generated from two focal spot positions spaced apart from each other in a first stereo-direction transverse to a viewing direction;

an X-ray detector that detects the generated X-ray radiation;
a processor that computes monoscopic and stereoscopic X-ray image data based on the X-ray radiation detected by the X-ray detector, and
a display device that displays the computed monoscopic and stereoscopic X-ray image data of the object with a gradual transition between the monoscopic viewing and the stereoscopic viewing.

* * * * *